United States Patent [19]

Perella et al.

[11] Patent Number: 6,004,914
[45] Date of Patent: Dec. 21, 1999

[54] AMPHOTERIC DERIVATIVES OF ALIPHATIC POLYAMINES WITH FATTY ACIDS, ESTERS OR TRIGLYCERIDES, WHICH ARE USEFUL FOR VARIOUS CONSUMER PRODUCTS AND INDUSTRIAL APPLICATIONS

[75] Inventors: James e. Perella, Mahwah; Joseph A. Komor, Ramsey, both of N.J.; Richard D. Katstra, Warwick, N.Y.

[73] Assignee: Mona Industries, Inc., Paterson, N.J.

[21] Appl. No.: 09/136,936

[22] Filed: Aug. 20, 1998

[51] Int. Cl.$^6$ .................. C11D 3/32; C11D 1/88
[52] U.S. Cl. .............. 510/126; 510/130; 510/501; 510/502; 162/76; 554/52
[58] Field of Search ............... 510/477, 501, 510/515, 502, 126, 130; 162/76

[56] References Cited

U.S. PATENT DOCUMENTS

| | | | |
|---|---|---|---|
| 2,936,251 | 5/1960 | Garceau et al. | 117/139.5 |
| 3,366,671 | 1/1968 | Cowen et al. | 260/501.12 |
| 5,643,864 | 7/1997 | Li et al. | 510/499 |
| 5,656,586 | 8/1997 | Li et al. | 510/535 |

OTHER PUBLICATIONS

R. Qu et al., Riyong Huaxue Gongye May 1996, 5, 15–16 (abstract).

R. Qu et al. Shandong Daxue Xuebao, Ziran Kexueban Jan. 1995, 1, 100–104 (abstract).

M. Shi et al. Riyong Huaxue Gongye Apr. 1992, 4, 184–187 (abstract).

M. Shi et al., Yukagaku Jan. 1993, 42, 49–51 (abstract).

M. Shi et al., Chinese Chemical Letters May 1992, 3, 347–348 (abstract).

*Primary Examiner*—Yogendra Gupta
*Assistant Examiner*—John R. Hardee
*Attorney, Agent, or Firm*—Franklyn Schoenberg; Norman E. Lehrer

[57] ABSTRACT

Amphoteric derivatives of aliphatic polyamines, such as diethylenetriamine or triethylenetetramine reacted with long chain fatty acids, esters or triglycerides from various natural or synthetic sources are effective in the softening/texture modification of substrates such as paper, textiles, human skin surfaces and hair tresses, as well as in applications for metal working and lubrication. The polyamines are first reacted with fatty acids, esters or triglycerides derived from various animal, vegetable or synthetic sources ranging in molecular distribution from butyric through erucic acids (e.g. milkfat, soy bean oil, rapeseed oil) to form polyamines or imidazolines; they are then further reacted with unsaturated or halogenated carboxylic acids, carboxylated epoxy compounds or acid anhydrides (e.g. acrylic acid, itaconic acid, chloroacetic acid, maleic anhydrides octadecenyl anhydride) to form the various amphoteric structures.

7 Claims, No Drawings

AMPHOTERIC DERIVATIVES OF ALIPHATIC POLYAMINES WITH FATTY ACIDS, ESTERS OR TRIGLYCERIDES, WHICH ARE USEFUL FOR VARIOUS CONSUMER PRODUCTS AND INDUSTRIAL APPLICATIONS

FIELD OF THE INVENTION

The present invention relates to amphoteric surface active agents, and more particularly to amphoteric derivatives of aliphatic polyamines, such as diethylenetriamine and triethylenetetramine reacted with long chain fatty acids, esters or triglycerides. In addition to being novel materials, the amphoteric derivatives of this invention are useful in a variety of applications including the softening/texture modification of substrates such as paper, textiles, human skin surfaces and hair tresses, as well as in applications for metal working, and lubrication.

BACKGROUND OF THE INVENTION

Amphoteric compositions of various types including derivatives of polyamines are known and have been used over the years for a variety of applications including surfactants in detergent and dishwashing formulations, fabric and paper treating compositions, metal treating and corrosion inhibition, and the like. For example, U.S. Pat. No. 2,999,069 to Masci teaches detergent compositions containing amphoteric derivatives of amidoamines but does not teach or disclose diamide or polyamide compositions having a reactive secondary, internal nitrogen amine site which is carboxyalkylated as provided in the present invention. Liquid dishwashing compositions disclosed in European Patent Application No. 92 203 230.5 to Jadwiga Palicka include amphoteric surface active agents; however, neither diamide nor polyamide compositions having a secondary, internal nitrogen amine site which is carboxyalkylated are disclosed by Palicka. U.S. Pat. No. 5,322,630 to Williams et al. discloses amphoteric derivatives of a broad range of fatty polyamines, fatty amidoamines, fatty imidazoline amines and polyamines which are employed as oilfield corrosion inhibitors. There is, however, no disclosure or suggestion in the Williams patent of the applications of the amphoteric derivatives of the polyamines herein disclosed, including neither the softening/texture modification of substrates such as paper, textiles, human skin surfaces and hair tresses, nor applications for metal working and lubrication.

Furthermore, providing non-irritating softening agents for fabric or paper substrates, or to human skin or hair, has been a long felt need. Fabrics tend to become slightly harsher after wear and laundering. Moreover, untreated personal hygiene facial tissue paper may be harsh and irritating to inflamed tissues, such as nasal orifice skin.

Various attempts have been made to soften fabrics such as suggested in patents directed to fabric softeners, for example, U.S. Pat. No. 3,904,533 of Neiditch for a liquid fabric softener, and U.S. Pat. Nos. 4,237,155 of Kardouche and 5,376,287 of Borcher et al which describe antistatic fabric softener sheets, which include fabric-softening agents, such as cationic and nonionic surfactants.

OBJECTS OF THE INVENTION

It is therefore an object of the present invention to define a family of amphoteric compounds comprising derivatives of aliphatic polyamines such as diethylenetriamine and triethylenetetramine wherein the polyamines are first converted to polyamides or imidazoline/amide derivatives thereof.

A further object of the present invention is to define and describe a process by which the above described amphoteric derivatives of aliphatic polyamides [ADAPS] may be made.

It is another object of the present invention to provide an effective softener for various substrates which might contact human skin, as well as skin and hair substrates themselves.

It is a still further object of the present invention to provide amphoteric surface active agents for use in other applications, such as metal working, lubricating, etc.

SUMMARY OF THE INVENTION

The present invention relates to amphoteric derivatives of aliphatic polyamines [ADAPS] that have important industrial and personal care uses, such as, for example, softeners, lubricants, and conditioners, etc. The ADAPs comprise derivatives of compositions which are intermediate aliphatic polyamides or imidazolines, and preferably aliphatic diamides, containing more than one substituent moiety selected from the group consisting of long alkyl chain fatty acids, esters and triglycerides, such as derived from animal, vegetable or synthetic sources ranging in molecular distribution from butyric through erucic acids. (e.g. milkfat, soybean oil, rapeseed oil).

The intermediate amide compound is then converted into an amphoteric compound by reacting it with unsaturated carboxylic acids, halogenated carboxylic acids, carboxylated epoxy compounds or in the case of the higher polyamines, acid anhydrides or polycarboxylic acids.

The carboxyalkylation step of the present invention attaches an alkyl carboxylic acid functional group to at least one secondary internal amine nitrogen atom, thereby forming the amphoteric products of the present invention. The amphoteric product is thus a polyamide or imidazoline derivative of the aliphatic polyamine starting material.

Compounds containing acidic functional groups suitable for use in reacting with aliphatic polyamides in accordance with the present invention include alkyl carboxyl groups [i.e., carboxylic acid functional moiety, COOH] where the carboxylic acid is derived from one or more unsaturated or halogenated carboxylic acids, carboxylated epoxy compounds, acid anhydrides and/or polycarboxylic acids with the proviso that the amphoteric composition must contain at least one ionizable nitrogen site. For the purposes of the present invention such above-mentioned unsaturated carboxylic acids, halogenated acids, carboxylated epoxy compounds, acid anhydrides or polycarboxylic acids, comprise an amphoteric forming group because the product produced by reacting with one of the acids is an amphoteric product.

DETAILED DESCRIPTION OF THE INVENTION

Consistent with the above discussion, a first specific group of ADAPs of the present invention may comprise amphoteric derivatives of diethylenetriamine [DETA] wherein the amphoteric derivatives of the present invention are prepared by first reacting DETA as a starting material with at least one member selected from long-alkyl-chain plant, animal or synthetic derived fatty acids, esters and triglycerides, such as, for example, compositions containing substituted or unsubstituted, branched or straight chain, saturated or unsaturated alkyl chain groups ranging in molecular distribution from butyric through erucic acids, that is, containing from 3 to 21 carbon atoms in addition to the carbonyl group.

An intermediate substituted DETA predominately diamide (preferably) or polyamide is thus formed having fatty alkyl moieties of 3 to 21 carbon atoms.

Amphoteric forming agents suitable for use in reacting with aliphatic polyamides in accordance with the present invention include alkyl carboxyl groups (i.e., carboxylic acid functional moiety, COOH] where the carboxylic acid is one or more unsaturated or halogenated carboxylic acids, or carboxylated epoxy compounds. Exemplary suitable amphoteric forming agents include vernolic acid, acrylic acid, itaconic acid, chloroacetic acid, maleic anhydride, octadecenyl anhydrides and adipic acid.

The ADAPS of the present invention also comprise a second group of compounds analogous to the above described DETA derivatives, that are amphoteric derivatives of triethylene tetramine [TETA]. The foregoing discussion applies to TETA just as it does to DETA.

As with the DETA derivatives, the amphoteric TETA derivatives also have more than one substituent which includes those derived from long alkyl-chain plant, animal or synthetic derived fatty acids, esters and triglycerides, ranging in molecular distribution from butyric through erucic acids (4–22 carbon atoms) with long length fatty alkyl amide moieties having from 3 to 21 carbon atoms.

In the case of higher polyamides the polyamide TETA derivatives are made amphoteric by reacting them with a member of the above-discussed amphoteric forming agent group, consisting of unsaturated carboxylic acids, halogenated carboxylic acids, carboxylated epoxy compounds, acid anhydrides and polycarboxyolic acids. Some typical examples include vemolic acid, acrylic acid, itaconic acid, chloroacetic acid, maleic anhydride, octadecenyl anhydride and adipic acid.

A third group of products having novel applications is comprised of amphoteric imidazolines which are prepared according to the method hereinafter described for preparation of the DETA, TETA or other polyamines.

The following general structural formulas numbered 1 through 4 comprise the novel compounds of the present invention, and are further exemplified and represented in Tables 1 and 2 below.

Formula 1, below, generically shows diethylenetriamine [DETA] amphoteric derivatives more particularly set forth in Table 1 below. Formula 1 is a diamide, having an amide group at each end of the molecule. The central (secondary) nitrogen site on the molecule is acidified to form the amphoteric end product of the present invention.

FORMULA 1

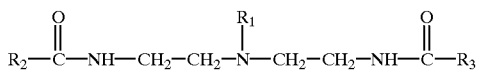

wherein:

$R_1$ is a saturated or unsaturated aliphatic mono or poly carboxylic acid moiety having one or more carbonyl functional groups derived from intermediates containing olefinic, halogenated or epoxy reactive sites, and may have one or more branched saturated or unsaturated, substituted or unsubstituted aliphatic chains containing from 2 to 18 carbon atoms; and $R_2$ and $R_3$, which may be the same or different, can be a straight or branched, saturated or unsaturated, substituted or unsubstituted alkyl chain of 3 to 21 carbon atoms.

Formula 2, below is a generic DETA-derived imidazoline, where the acidic functional group making the molecule amphoteric is attached to the quaternary nitrogen. Formula 2 is more particularly set forth in Table 1 below.

FORMULA 2

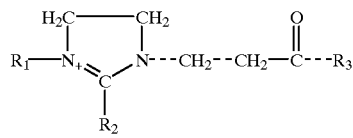

wherein:

$R_1$ is a saturated or unsaturated aliphatic mono or poly carboxylic acid moiety having one or more carbonyl functional groups derived from intermediates containing olefinic, halogenated or epoxy reactive sites, and may have one or more straight or branched, saturated or unsaturated, substituted or unsubstituted aliphatic chains containing from 2 to 18 carbon atoms; and $R_2$ and $R_3$, which may be the same or different, can be a straight or branched, saturated or unsaturated, substituted or unsubstituted alkyl chain of 3 to 21 carbon atoms.

Formula 3, below, is similar to Formula 1, except that Formula 3 shows a generic triethylenetetramine [TETA] amphoteric diamide. Formula 3 is more particularly set forth in Table 2 below. The discussion of Formula 1 above applies to Formula 3, except that Formula 3 initially has two secondary amine nitrogen atom sites. At a minimum one of these secondary amine sites must be acidified but both may be so acidified to create the amphoteric end product.

FORMULA 3

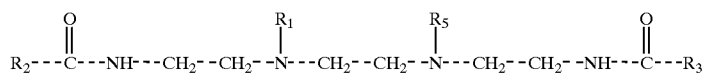

wherein:

$R_1$ is a saturated or unsaturated aliphatic mono or poly carboxylic acid moiety having one or more carbonyl functional groups derived from intermediates containing olefinic, halogenated, epoxy or anhydride reactive sites, and may have one or more straight or branched, saturated or unsaturated, substituted or unsubstituted aliphatic chains containing from 2 to 18 carbon atoms;

$R_2$ and $R_3$, which may be the same or different, can be a straight or branched, saturated or unsaturated, substituted or unsubstituted alkyl chain of 3 to 21 carbon atoms; and $R_5$ may be hydrogen, the same or different from $R_1$, with the proviso that both may not be simultaneously derived from anhydride intermediates. $R_5$ when different from $R_1$, may be derived from any appropriate alkylating group.

Formula 4, below, is similar to Formula 2, except that Formula 4 shows a generic triethylenetetramine [TETA] amphoteric polyamidoamine or amidoimidazoline amphoteric. Formula 4 is more particularly set forth in Table 2 below. Except for the fact that Formula 4 is TETA derived rather than DETA derived, the discussion of Formula 2 above applies to Formula 4.

FORMULA 4

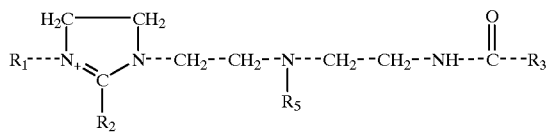

wherein:
- $R_1$ is a saturated or unsaturated aliphatic mono or poly carboxylic acid moiety having one or more carbonyl functional groups derived from intermediates containing olefinic, halogenated or epoxy reactive sites, and may have one or more straight or branched, saturated or unsaturated, substituted or unsubstituted aliphatic chains containing from 2 to 18 carbon atoms;
- $R_2$ and $R_3$, which may be the same or different, can be straight or branched, saturated or unsaturated, substituted or unsubstituted alkyl chain of 3 to 21 carbon atoms; and
- $R_5$ may be hydrogen, the same as $R_1$ or may be a straight or branched, saturated or unsaturated, substituted or unsubstituted alkyl chains having 3 to 21 carbon atoms derived from any appropriate alkylating group including anhydrides.

TABLE 1

Polyamine-Derived Amphoterics
DETA Derivatives

I
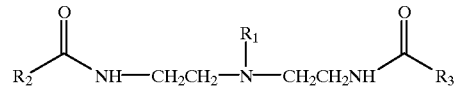

II
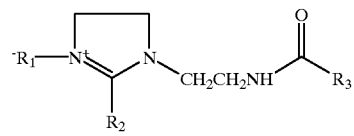

III
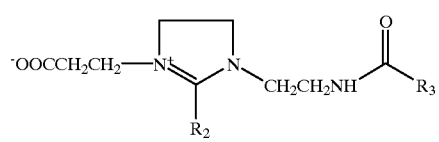

A      B      C
where $R_1$ = $CH_2COOH$ or $CH_2CH_2COOH$ or 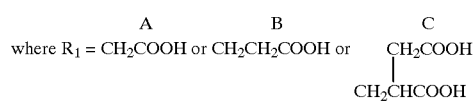

G      H
where $R_2$ & $R_3$ = $C_2H_5$ to $C_{22}H_{45}$ or $C_2H_4$ to $C_{18}H_{36}$

TABLE 2

Polyamine-Derived Amphoterica
TETA Derivatives

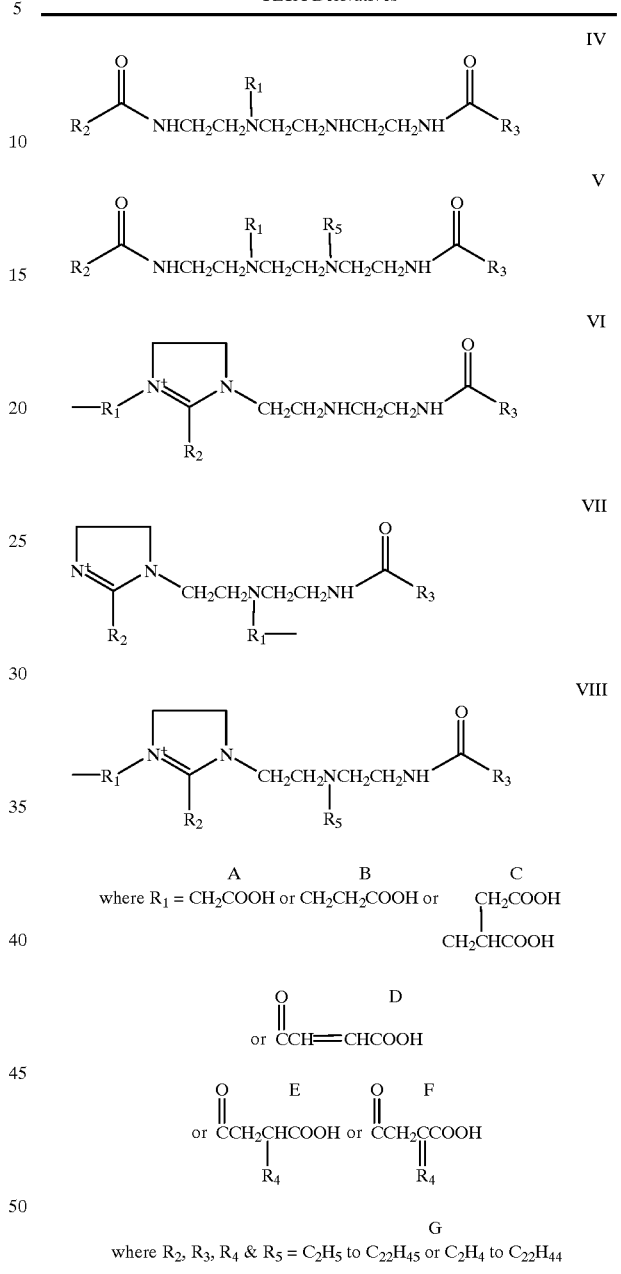

The DETA and TETA polyamide and imidazoline-amide intermediate compositions suitable for use in the preparation of amphoteric compositions of the present invention in accordance with the practice of the invention are well known and include those derived from substituted or unsubstituted, branched or straight chain, saturated or unsaturated fatty acids, esters, or triglycerides with fatty alkyl amide moieties containing from 4 to 22 carbon atoms. Examples of suitable fatty acids, esters or triglycerides include octanoic acid, decanoic acid, lauric acid, myristic acid, palmitic acid, stearic acid, oleic acid, linoleic acid, linolenic acid, methyl esters or glyceride esters of such acids or mixtures thereof as are found in coconut oil, palm oil, sunflower oil, soybean oil, rapeseed oil, castor oil, fish oil, tallow fat, milk fat, lard and other natural sources or may be of synthetic origin.

The materials of the present invention are embodied in reactions carried out under the following conditions, as noted in the Examples below.

For example, amphoterics are derived from DETA-diamides, such as shown in Example 1 below, wherein linoleic-DETA diamide monopropionate is produced, from a reaction wherein soybean oil and diethylenetriamine are first mixed. In a second reaction, acrylic acid is added.

In Example 2 below, oleic DETA diamide is produced from a mixture of olive oil and diethylenetriamine.

In Example 3 below, to the amide of example 2 there is added acrylic acid, to produce oleic DETA diamide monopropionate, or, as noted in Example 4 below, there is added itaconic acid, to produce oleic DETA diamide mono-3-carboxybutyrate.

As noted in Example 5 below, caprylic-capric-DETA diamide propionate is produced from the reaction of a mixture of caprylic-capric triglyceride and diethylenetriamine, which is further reacted with acrylic acid.

Furthermore, as noted in Example 6 below, dioleyl-imidazoline-amide-propionate is produced from two reactions, namely a reaction of a mixture of oleic acid and diethylenetriamine, which is further reacted with glacial acrylic acid.

The foregoing present invention includes aliphatic intermediate derivatives of polyamine compounds resulting in amphoteric imidazolines, polyamides, and preferably diamides having a carboxyalkylated secondary, internal amine nitrogen site. Carboxyalkylation is achieved by reacting a substituted polyamine or polyamide intermediate with an amphoteric-forning group consisting of halogenated carboxylic acids, unsaturated carboxylic acids, suitable epoxy compounds, or anhydrides in the case of higher polyamines such as TETA.

The resulting compounds are useful as softeners for tissues, fabrics, hair and skin, and a novel method of softening is disclosed based on the use of the compounds described herein. Because the novel compounds of the present invention provide antiwear properties, a method of using these compounds of the present invention in metal working is also taught.

It is therefore a further aspect of the invention to use the amphoteric derivative compositions of the invention, for example, as softening agents for facial tissue paper, textiles, hair and human skin in amounts of 0.1 to 10% by weight and for metal working applications such as lubricating and antiwear compositions in amounts of from about 0.1% by weight.

The invention is noted in the following illustrative examples, which are provided herein for the purposes of illustration only, and are not intended to limit the scope of the present invention, as noted in the appended claims.

Pertinent examples of preparation of the novel materials of the present invention are embodied in reactions carried out under the following conditions.

EXAMPLE 1

Linoleic-DETA Diamide Monopropionate

To a three-necked flask fitted with a stirrer, thermometer and reflux condenser is charged 584.0 gms. soybean oil and 103.0 gms. [DFTA] diethylenetriamine. The reaction mixture is heated at 180–190° C. for four hours, at which time the alkali value drops to 90 (mm KOH/g). After cooling to 70° C., 79.2 gms. acrylic acid was added. The addition is exothermic and the temperature rises to 102° C. The temperature is maintained at 90–100° C. for an additional four hours. After the reaction is complete, the final alkali value is 75, the acid value is 64 and the 10% pH in isopropyl alcohol/water is 4.8.

EXAMPLE 2

Oleic-DETA-Diamide

To a three-necked flask fitted with a stirrer, thermometer and reflux condenser is charged 584.0 gms olive oil and 103.0 gms diethylenetriamine [DETA]. The reaction mixture is heated at 180–190° C. for four hours at which time the alkali value drops to 90 (mm KOH/g).

EXAMPLE 3

Oleic-DETA Diamide-Monopropionate

To 68.7 gms of the amide of above Example 2 at 90° C., in a reaction vessel is charged 7.9 gms of acrylic acid. The mixture is heated with agitation at 95–105° C. for five hours until reaction is complete, as evidenced by disappearance of acrylic acid.

EXAMPLE 4

Oleic-DETA Diamide Mono-3-Carboxybutyrate

To 68.7 gms of the amide of Example 2 at 90° C. is charged 14.3 gms of solid itaconic acid. The mixture is heated with agitation at 95–105° C. for 5 hours, until reaction is complete, as evidenced by disappearance of itaconic acid.

EXAMPLE 5

Caprylic-Capric-DETA Diamide Propionate

To a three-necked flask fitted with a stirrer, thermometer and reflux condenser there is charged 330 gms of a caprylic capric-triglyceride, of the trade name Neobee M5, from Stepan Chemical Co., and 103 gms of diethylenetriamine. The mixture is heated at 180–185° C. for four hours, after which the alkali value dropped to 135 (mm KOH/g). After cooling to 70° C., 72 gms of acrylic acid are added and the mixture heated at 90–100° C. for four hours, until the reaction is complete, as evidenced by disappearance of acrylic acid.

EXAMPLE 6

Dioleyl-Imidazoline-Amide-Propionate

To a three-necked flask fitted with a stirrer, thermometer and distillation condenser there is charged 564 gms. of oleic acid and 103.2 gms of diethylenetriamine. The reaction mixture is heated to 155° C. where water of reaction begins to distill. The temperature is allowed to rise gradually to 190–200° C. over about three hours at which time the alkali value is 105.6 and the acid value is 4. 10. Vacuum was then applied gradually until a pressure of 11 mm Hg is reached. Samples are taken periodically and checked for imidazoline content. After about three hours at 190° C. and 11 mm Hg, an imidazoline content of 90% is obtained. The product is then cooled to 70° C. and the vacuum is released. 72 gms of glacial acrylic acid is added. The exothermic reaction carried the temperature to 95° C., which is maintained for an additional 4 hours, until reaction is complete.

EXAMPLE 7

Milk Lipids—DETA Diamide Monopropionate

To a three-necked flask fitted with a stirrer, thermometer and reflux condenser is charged 490 gms. milk lipids and 103.0 gms. of diethylenetriamine (DETA). The reaction mixture is heated at 180–190° C. for four hours, at which time the alkali value drops to 93 (mm KOH/g). After cooling to 70°, 72 gms of acrylic acid is added. The addition is exothemic and the temperature rises to 102° C. The temperature is maintained at 90–100° C. for an additional four hours. After the reaction is complete, the final alkali value is 88, the acid value is 76 and the 10% pH in isopropyl alcohol/water is 65.

EXAMPLE 8

Milk Lipids-Imidazoline-Amide Dipropionate

To a three-necked flask fitted with a stirrer, thermometer and reflux condenser is charged 490 gms of milk lipids and 103 gms of diethylenetriamine (DETA). The reaction mixture is heated at 155° C. where water of reaction begins to distill. The temperature is allowed to rise gradually to 190–200° C. over about three hours, at which time the alkali value is 96 (mm KOH/g).

Vacuum is then applied gradually until a pressure of 11 mm of Hg is reached. Samples are taken periodically and checked for imidazoline content. After about three hours at 190° C. and 11 mm Hg, an imidazoline content of 90% is obtained. The product is cooled to 70° C. and the vacuum is released.

To the molten imidazoline is added 172 gms of methylacrylate and the mixture is heated at 90 to 100° C. for four hours. After which the methylacrylate content is less than 5%. The reaction mixture is charged to a separate flask containing a solution of 120 gms of 50% caustic soda, 522 gms of propylene glycol and 729 gms of water and heated at 90° to 95° C. for two hours to hydrolyze the methyl ester. After cooling to 50° C., the reaction product is a clear amber liquid with total solids of 34.6% having a 10% pH in isopropyl alcohol/water of 10.1.

EXAMPLE 9

Table #3 below outlines the procedure used, as well as the results obtained in evaluating several diethylenetriamine (DETA) amphoteric derivatives (Samples A-1, A-2, A-3 and A-4) for their softening properties on tissue paper.

The results of Table #3 indicate that all of the DETA-derived amphoterics tested (Samples A-1, A-2, A-3 and A-4) exhibited very good paper softening properties and are superior to the Control Sample 1, namely, a DETA imidazolinium quaternary derivative tested.

The amphoteric derivatives, Samples A- 1, A-2, A-3 and A-4 in Table #3, are found to be very effective in softening challis wool swatches which are soaked in aqueous dispersions of the amphoterics and then rinsed and allowed to dry using the procedure similar to that used with facial tissue paper. It is also noted that the amphoteric deriative samples are effective in depositing a residual, smooth conditioned feeling to human skin and hair.

TABLE #3

FACIAL TISSUE SOFTNESS EVALUATIONS OF DIFTHYLENETRIAMINE (DETA) DERIVATIVES

Procedure:
1. 1% active test solutions/dispersions are prepared in deionized water and adjusted with lactic acid to the 4–8 pH range.
2. Evaluations are conducted using 8"×9" untreated paper tissues weighing approximately 1.5 grams each. The lower half of each tissue is dipped briefly into the 1% active solution being tested, then the tissues are withdrawn, allowed to drain, dried and equilibrated for several hours at ambient temperature and humidity. A deionized water blank is included in the test regimen.
3. Treated tissues are evaluated (undipped versus dipped portions) and ranked for softness by a small R&D expert panel. Numerical softness rankings are assigned as follows:

0=Poor/harsh texture

1=Fair

2=Good

3=Very Good

4=Excellent/very soft texture

After Dipping in 1% Active Dispersions
Followed by Draining and Drying

| | 1% Active in Water Material Tested | Softness/Texture |
|---|---|---|
| Sample A-1 | Milkfat DETA Imidazolinium Amphomonopropionate | 3.5 |
| Sample A-2 | Soybean Oil DETA Diamide Amphomonopropionate | 3.5 |
| Sample A-3 | Rapeseed Oil DETA Diamide Amphomonopropionate | 3 |
| Sample A-4 | Milkfat DETA Imidazolinium Amphomonopropionate | 3/3.5 |
| Control 1 | Milkfat DETA Imidazolinium Quaternary | 2.5 |
| Control 2 | Deionized Water Blank | 0 |

All of the DETA amphoteric derivatives tested exhibit very good paper softening properties and are superior to the quaternary softener (Control 1).

EXAMPLE 10

Table #4 below shows a comparison of two DETA-derived amphoterics, Sample B-1, namely, a disoya DETA amphomonopropionate as prepared in Example 1 and Sample B-2, namely, a di-caprylic-capric DETA amphomonopropionate as prepared in Example 5 versus a Control, namely, a commercial milk lipid amido propyl betaine, when used in a bath and shower cleanser. The DETA derivatives of Samples B-1 and B-2 exhibite better conditioning on skin and hair, and better foam in the case of the caprylic-capric amphoteric than the Control, namely, milk lipid amido-propyl betaine.

TABLE 4

Bath and Shower Cleansers
Soya & C8–10 DETA Diamide Amphoterics
vs
Milk Lipid Amidopropyl Betaine

| Raw Material | R67.00-11A % by Weight | R6700-11B % by Weight | R70.01-127 % by Weight |
|---|---|---|---|
| Deionized Water | 45 | 45 | 45 |
| Sodium Chloride | 1 | 1 | 1 |
| Sodium Lauryl Sulfate (28%) | 10 | 10 | 10 |
| MONALAC MPL | 2 | 2 | 2 |
| MONALAC MO | 2 | 2 | 2 |
| Sodium Laureth Sulfate (26%) | 35 | 35 | 35 |

TABLE 4-continued

Bath and Shower Cleansers
Soya & C8–10 DETA Diamide Amphoterics
vs
Milk Lipid Amidopropyl Betaine

| Raw Material | R67.00-11A % by Weight | R6700-11B % by Weight | R70.01-127 % by Weight |
|---|---|---|---|
| Milk Lipid Amidopropyl Betaine (MONALAC MAB) Control | 5 | — | — |
| Sample B-1 (Example 1) | — | 5 | — |
| Sample B-2 (Example 5) | — | — | 5 |
| The ingredients are added in the order listed. The pH is adjusted to 6.0–6.5 and desired preservatives, fragrances, etc. are added. | | | |
| Appearance: | Clear Liquid | Clear yellow Liquid | Opaque, Light Yellow Liquid |
| Viscosity (ambient temp.): | 2,000 cps | 1,500 cps | 1000 |
| Viscosity with an additional 0.25% NaCl: | 6,500 cps | 3,500 cps | 800 |
| pH: | 6.37 | 6.38 | 6.36 |

After washing, all of the products give a very smooth conditioned feel to the skin and hair, but the di-soya and di(C8-10) amphoterics, Sample B-1 and B-2, exhibit a higher level of smoothness than the milk lipid amidopropyl betaine. In addition, the di(C8-10) amphoteric (Sample b-2) exhibits much higher foam levels during washing.

Further application testing is carried out on polyamine amnphoteric derivatives of the present invention in the areas of lubrication, hydraulic fluids, metalworking and anti-wear additives.

EXAMPLE 11

Table #5 below shows a list of Samples C-1 through C-8 tested for metal working, lubrication and anti-wear additives. The "structure type" refers to the chemical structure noted in Tables 1 and 2 herein, wherein the Roman numerals refer to the basic molecular structure and the Alphabetical designations refer to the specific designations for the various "R" groups in the formulas of Tables 1 and 2. Performance data are shown for experimental compositions evaluated in the zwitterionic acid forms, as well as the long chain alkylamine salts.

TABLE 5

DESCRIPTIONS OF SAMPLES TESTED
For Metalworking & Hydraulic Fluid Additives

| Sample Designation | Structure Type | $R_2$ & $R_3$ | Acid Form or Neutralizing Agent |
|---|---|---|---|
| C-1 | I-A | $C_{17}H_{34}$ | Acid Form |
| C-2 | III | $C_{17}H_{34}$ | Tridecyloxypropylamine |
| C-3 | III | $C_{17}H_{34}$ | Acid Form |
| C-4 | I-C | $C_{17}H_{34}$ | Acid Form |
| C-5 | I-C | $C_{17}H_{34}$ | Tridecyloxypropylamine |
| C-6 | I-B | $C_{17}H_{34}$ | Tridecyloxypropylamine |
| C-7 | I-C | $C_{17}H_{34}$ | Tridecyloxypropylamine |
| C-8 | I-B | Soya | Acid Form |

Table #6 below shows that in ASTM 2783 studies of blends with paraffinic and naphthenic derived mineral oils, marked decreases in coefficients of friction and steel ball scar diameters are noted for several of these derivatives.

TABLE 6

Results of Four-Ball Method Testing (ASTM D2783)

| Sample Tested @ 0.1% in Mineral Oil | Coefficient of Friction | Scar Diameter (mm.) | 2% ZnDTP Added to 0.1% in Mineral Oil | Coefficient of Friction | Scar Diameter (mm.) |
|---|---|---|---|---|---|
| C-6 | 0.0493 | 0.9 | C-6 | 0.0586 | 0.5 |
| C-7 | 0.0595 | 0.9 | C-7 | 0.0510 | 0.4 |
| C-2 | 0.0595 | 0.9 | C-2 | 0.0782 | 0.5 |
| C-1 | 0.0833 | 0.7 | C-1 | 0.0510 | 0.5 |
| C-5 | 0.0935 | 0.8 | C-5 | 0.0773 | 0.5 |
| Monacor 39* | 0.0799 | 0.5 | Monacor* 39 | 0.0595 | 0.5 |
| | | | ZnDTP alone | 0.0952 | 0.6 |

*Commercial test products
**Zinc dialky dithio phosphate

We claim:
1. Texture and softening compositions for paper and textile substates, as well as human hair and skin comprising amphoteric compositions that are represented by the formula:

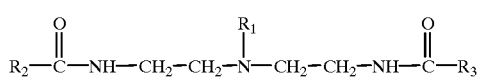

wherein:

$R_1$ is an unsaturated aliphatic mono or poly carboxylic acid moiety having one or more carboxyl functional groups derived from intermediates containing olefinic or carboxylated epoxy reactive sites, and having one or more straight or branched, saturated or unsaturated aliphatic chains containing from 2 to 18 carbon atoms; and $R_2$ and $R_3$, which may be the same or different, are a straight or branched, saturated or unsaturated alkyl chains of 3 to 21 carbon atoms.

2. Texture and softening compositions as in claim 1, wherein further $R_1$ is derived from a carboxylic acid having an unsaturated alkyl carbon chain.

3. Texture and softening compositions as in claim 1 represented by the general Formula as set forth below:

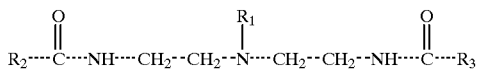

wherein:

$R_1$ is an unsaturated aliphatic, mono or poly carboxylic acid moiety having one or more carboxyl functional groups derived from intermediates containing olefinic reactive sites, having one or more straight or branched, saturated or unsaturated aliphatic chains containing from 2 to 18 carbon atoms; and $R_2$ and $R_3$, which may be the same or different, are straight or branched, saturated or unsaturated alkyl chain of 3 to 21 carbon atoms.

4. A method of softening paper, textile and human substrates comprising contacting the substrate to be softened with compositions comprising an effective amount of the compostions of claim 1; and, permitting the contacted substrate to dry.

5. The method of claim 4 wherein the substrate to be softened is paper.

6. The method of claim 4 wherein the substrate to be softened is textile fabric.

7. Metal treating compositions comprising an effective amount of the composition of claim 1.

* * * * *